United States Patent [19]

Hogan

[11] Patent Number: 5,453,357
[45] Date of Patent: Sep. 26, 1995

[54] PLURIPOTENTIAL EMBRYONIC STEM CELLS AND METHODS OF MAKING SAME

[75] Inventor: Brigid L. M. Hogan, Brentwood, Tenn.

[73] Assignee: Vanderbilt University, Nashville, Tenn.

[21] Appl. No.: 958,562

[22] Filed: Oct. 8, 1992

[51] Int. Cl.⁶ ............................... C12N 5/06; C12Q 1/02
[52] U.S. Cl. ............................ 435/7.21; 435/21; 435/29; 435/34; 435/240.2; 435/240.21; 435/240.3
[58] Field of Search ....................... 435/7.21, 29, 240.2, 435/240.21, 240.3, 21, 34

[56] References Cited

U.S. PATENT DOCUMENTS 5,166,065  11/1992  Williams et al. .................... 435/240.1
5,340,740   8/1994  Petitte et al. ......................... 435/240.2

FOREIGN PATENT DOCUMENTS

WO90/03432  4/1990  WIPO.

OTHER PUBLICATIONS

Piedrahita et al., *Theriogenology* 29:286 (Jan. 1988).
Handyside et al., *Roux's Arch. Dev. Biol.* 196:185–190 (1987).
Flake et al., *Science* 233:776–778 (Aug. 15, 1986).
Ware et al., Biology of Reproduction Supp. 38:129 (1988).
Robertson et al. *Nature* 323:445–448 (1986).
Labosky et al., *1994 Germline development*, Wiley, Chichester (Ciba Foundation Symposium 182) ,pp. 157–178.
Lapidot et al., *Science* 255:1137–1141 (1992).
Anne McLaren, *Nature* 359:482–483 (1992).
Reynolds & Weiss, *Science* 255:1707–1710 (1992).
Snouwaert et al., *Science* 257:1083–1088 (1992).
Erwin F. Wagner, *The EMBO Journal*, 9:3025–3032 (1990).
Stemple and Anderson, *Cell* 71:973–985 (1992).
Jones et al., *Nature* 347:188–189 (1990).
Resnick et al., *Nature* 359:550–551 (1992).
Evans and Kaufman, *Nature* 292:154–156 (1981).
Martin, *PNAS* 78:7634–7638 (1981).
Bradley et al., *Nature* 309:255–256 (1984).
Rathjen, *P.D. Genes Dev.* 4:2308–2318 (1990).
Rathjen, *Cell* 62:1105–1114 (1990).
De Felici and McLaren, *Exp. Cell. Res.* 144:417–427 (1983).
Wabik–Sliz and McLaren, *Exp. Cell. Res.* 154:530–536 (1984).
Donovan et al., *Cell* 44:831–838 (1986).
Dolci et al., *Nature* 352:809–811 (1991).
Matsui et al., *Nature* 353:750–752 (1991).
Stewart and Mintz, *Proc. Nat'l. Acad. Sci. U.S.A.* 78:6314 (1981).
Mintz et al, *Proc. Nat'l. Acad. Sci. U.S.A.* 75:2834–2838 (1978).
Noguchi and Stevens, *J. Natl' Cancer Inst.* 69:907–913 (1982).
Ginsburg et al., *Development* 108:521–528 (1990).
Monk et al., *Development* 99;371–382 (1987).
Godin et al., *Nature* 352:807–808 (1991).
Matsui et al., *Cell* 70:841–847 (1992).
E. Notarianni et al., *Journals of Reproduction & Fertility Supplement* 41:51–56, abstract, 1990.
A. Smith et al., *Nature* 336:688–690, abstract, 1988.
C. Mummery et al., *Cell Differentiation and Development* 30:195–206, abstract, 1990.

*Primary Examiner*—David Saunders
*Attorney, Agent, or Firm*—Needle & Rosenberg

[57] ABSTRACT

The present invention provides a non-mouse pluripotential embryonic stem cell which can:

(a) be maintained on feeder layers for at least 20 passages; and (b) give rise to embryoid bodies and multiple differentiated cell phenotypes in monolayer culture. The invention further provides a method of making a pluripotential embryonic stem cell comprising administering a growth enhancing amount of basic fibroblast growth factor, leukemia inhibitory factor, membrane associated steel factor, and soluble steel factor to primordial germ cells under cell growth conditions, thereby making a pluripotential embryonic stem cell.

14 Claims, 5 Drawing Sheets

PLURIPOTENTIAL EMBRYONIC STEM CELLS AND METHODS OF MAKING SAME

This invention was made with government support under grant number HD25580-04 from the National Institute of Health Child Health and Development. The United States government has certain rights in the invention.

BACKGROUND OF THE INVENTION

1. Field of the Invention

This invention relates to pluripotential embryonic stem cells and methods and compositions for making pluripotential embryonic stem cells.

2. Background Art

Primordial germ cells (PGCs) in the mouse are thought to be derived from a small population of embryonic ectoderm (epiblast) cells set aside at the egg cylinder stage prior to gastrulation (Lawson and Pederson, 1992), or even earlier (Soriano and Jaenisch, 1986). By 7 days post coitum (p.c.) about 100 alkaline phosphatase (AP) positive PGCs can be detected in the extra embryonic mesoderm just posterior to the definitive primitive streak (Ginsberg et al., 1990). These cells continue to proliferate and their number increases rapidly to around 25,000 at 13.5 days p.c. (Mintz and Russell, 1957; Tam and Snow, 1981). At the same time the PGCs migrate from the base of the allantois along the hind gut and reach the genital ridges by 11.5 days p.c. In the genital ridge, PGCs stop dividing at around 13.5 days p.c., and enter either mitotic arrest in the developing testis or meiosis in the ovary. In a few strains of mice, e.g. 129, this normal program can be disrupted if the male genital ridge from an 11.5 to 12.5 days p.c. embryo is grafted to an ectopic site such as the testis or kidney capsule. Under these conditions some PGCs give rise to teratomas and transplantable teratocarcinomas containing pluripotential embryonal-carcinoma (EC) stem cells (Stevens and Makensen, 1961; Stevens, 1983; Noguchi and Stevens, 1982).

Previous studies have shown that steel factor (SF) and leukemia inhibitory factor (LIF) synergistically promote the survival and in some cases the proliferation of mouse PGCs in culture (Godin et al., 1991; Dolci et al., 1991; Matsui et al., 1991). However, under these conditions, PGCs have a finite proliferative capacity that correlates with their cessation of division in vivo. A similar finite proliferative capacity has been reported for oligodendrocyte-type 2 astrocyte (O-2A) progenitor cells in the rat optic nerve. In this case, PDGF is involved in the self renewal growth of O-2A cells (Noble et al., 1988; Raff et al., 1988). After a determined number of cell divisions, O-2A cells may lose their responsiveness to PDGF and start differentiating into oligodendrocytes. If both PDGF and basic fibroblast growth factor (bFGF) are added in culture, O-2A progenitor cells keep growing without differentiation (Bogler et al., 1990).

Since pluripotential embryonic stem cells (ES) can give rise to virtually any mature cell type they are of great value for uses such as creating genetically manipulated animals. However, it has previously been possible only to obtain ES cells from mice. These mice ES cells were obtained from cultures of early blastocytes. Attempts at isolating ES cells from other animals have failed. Therefore, there is a great need to produce and maintain ES cells from a variety of different animals.

The present invention satisfies this need by demonstrating that, in the presence of bFGF, SF and LIF, PGCs continue to proliferate in culture and give rise to colonies of ES cells. These stem cells can give rise to a wide variety of mature, differentiated cell types both in vitro and when injected into nude mice and when combined with embryos to form a chimera.

SUMMARY OF THE INVENTION

The present invention provides a non-mouse pluripotential embryonic stem cell which can:

(a) be maintained on feeder layers for at least 20 passages; and (b) give rise to embryoid bodies and multiple differentiated cell phenotypes in monolayer culture. The invention further provides a method of making a pluripotential embryonic stem cell comprising administering a growth enhancing amount of basic fibroblast growth factor, leukemia inhibitory factor, membrane associated steel factor, and soluble steel factor to primordial germ cells under cell growth conditions, thereby making a pluripotential embryonic stem cell.

(A) PGCs from 8.5 day p.pc. embryos were seeded into wells containing Sl/Sl$^4$ feeder cells either alone (open circles) or with soluble rSF (closed circles), soluble rSF and LIF (closed squares), or soluble rSF, LIF and bFGF (closed triangles). Cultures were fixed and the number of AP positive cells counted.

(B) As in (A) except that cells were cultured without added factors (open circles), with soluble rSF (closed circles), with bFGF (closed triangles) or with soluble rSF and bFGF (open triangles).

(C) As in (A) except that cells were cultured on Sl$^4$-m220 cells either alone (open circles) or with soluble rSF (closed circles), soluble rSF and LIF (closed squares), soluble rSF and bFGF (open triangles) and soluble rSF, LIF and bFGF (closed triangles).

Each experiment was carried out with duplicate wells and numbers are the means +s.e.m. of three separate experiments.

FIG. 2 shows the morphology of primary and secondary cultures of PGCs and their descendants. PGCs from 8.5 d p.c. embryos (A-E, G,H) or 12.5 d p.c. male genital ridges (F) were cultured on Sl$^4$-m220 cells as described and stained for AP activity.

(A) Primary culture after 4 days in the presence of LIF. Note that the AP positive cells are scattered among the feeder cells.

(B) Primary culture after 4 days in the presence of soluble rSF, LIF and bFGF. Note that the AP positive cells now form tight clumps.

(C) As for B, but after 6 days in culture.

(D) Secondary culture after 6 days in the presence of soluble rSF, LIF, and bFGF In this colony all the cells are AP positive.

(E) As for D except that cells at the edges of the colony are AP negative.

(F) PGCs from 12.5 day p.c. male genital ridge were cultured for 6 days in the presence of soluble rSF, LIF and bFGF. Colonies of tightly packed AP positive cells are present.

(G) Colony of ES-like cells in a secondary culture with soluble SF, LIF and bFGF stained with SSEA-1 monoclonal antibody and for AP activity. Phase contrast microscopy.

(H) The same colony as in G viewed by fluorescence microscopy. AP positive cells also express SSEA-1.

(I) Colony grown under same conditions as (G) but stained without primary antibody Scale bars=200 um.

Figure 3:
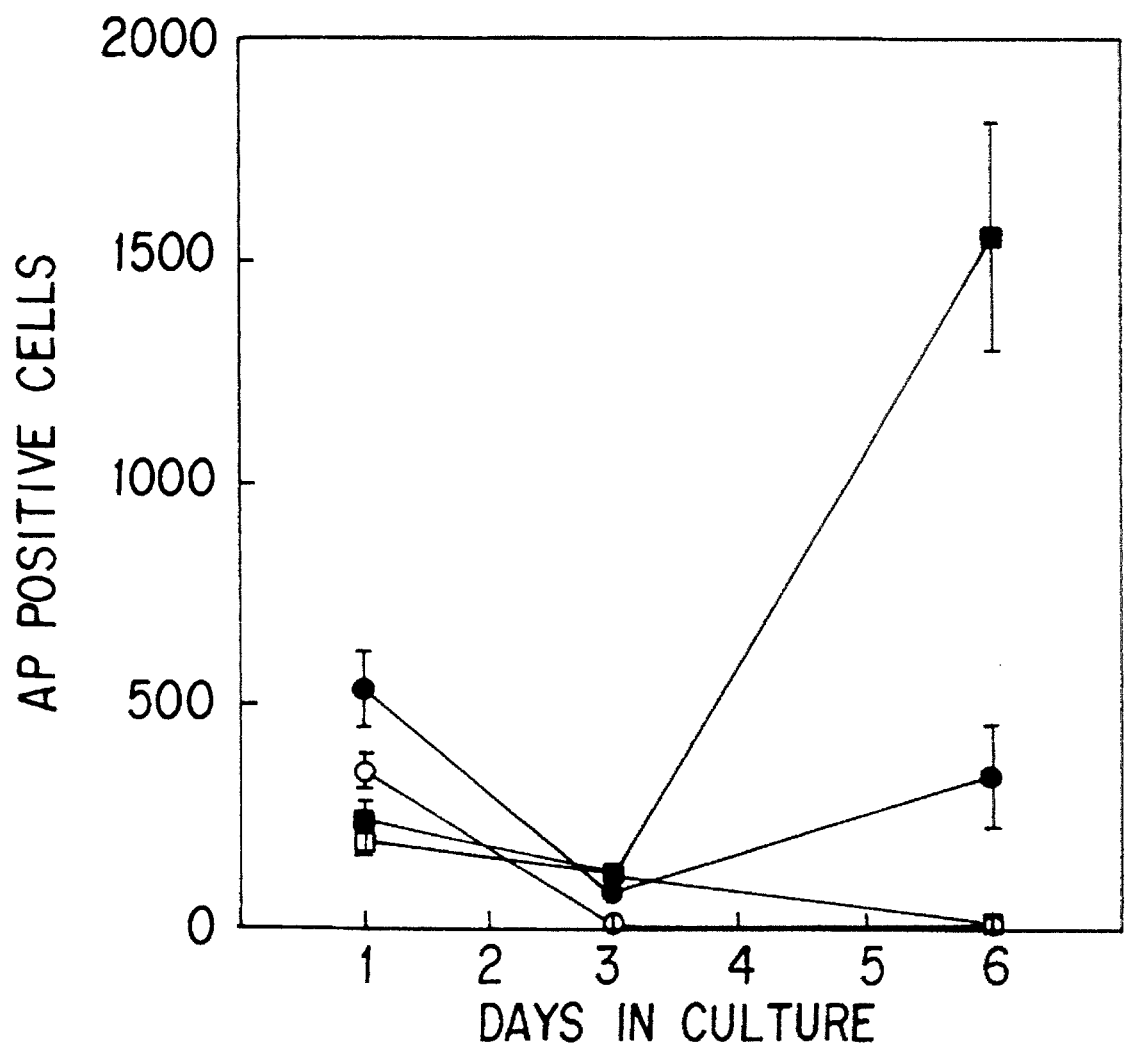
Figure 4B:
Figure 4A:
Figure 4E:
Figure 4D:
Figure 4C:

FIG. 3 shows the effect of growth factors on male and female PGCs in culture. Cells were dissociated from either male (squares) or female (circles) genital ridges from 12.5 day p.c. mouse embryos and cultured on Sl$^4$-m220 feeder cells either alone (empty symbols) or with soluble rSF, LIF and bFGF (filled symbols). Cells were fixed and the number of AP positive cells counted. The experiment was carried out three times, with duplicate wells.

FIG. 4 shows the morphology of undifferentiated PGC derived ES cells and their differentiated derivatives.

(A) Colony of densely packed ES-like cells obtained from PGCs of an 8.5 day p.c. embryo grown on Sl$^4$-m220 cells in the presence of soluble rSF, LIF and bFGF for 6 days. Scale bar=100 um.

(B) Simple embryoid bodies with an outer layer of endoderm (arrows) obtained after culturing PGC-derived ES cells for 4 days in suspension.

(C) Section of a teratoma obtained by injecting ES-like cells derived from PGCs of an 8.5 day p.c. embryo into a nude mouse. The region shown here contains neural tissue and pigmented epithelium. Scale bar=200 um.

(D) Region of the same tumor as in (C) showing a dermoid cyst and secretory epithelium.

(E) Region of the same tumor as in C and D, showing bone and cartilage. The differentiated tissues shown in C-E were seen in addition to other tissue types in multiple tumors from all three lines tested.

DETAILED DESCRIPTION OF THE INVENTION

The term "embryonic ectoderm" is used herein. "Embryonic ectoderm" and "epiblast" can be used interchangeably to refer to the same cell type.

A "pluripotential embryonic stem cell" as used herein means a cell which can give rise to many differentiated cell types in an embryo or adult, including the germ cells (sperm and eggs). This cell type is also referred to as an "ES cell" herein.

A "fibroblast growth factor" (FGF) as used herein means any suitable FGF. There are presently seven known FGFs (Yamaguchi et al. (1992)). These FGFs include FGF-1 (acidic fibroblast growth factor), FGF-2 (basic fibroblast growth factor), FGF-3 (int-2), FGF-4 (hst/K-FGF), FGF-5, FGF-6, and FGF-7. Each of the suitable factors can be utilized directly in the methods taught herein to produce or maintain ES cells. Each FGF can be screened in the methods described herein to determine if the FGF is suitable to enhance the growth of or allow continued proliferation of ES cells or their progenitors.

"Steel factor" (SF) is used herein. SF is also called stem cell factor, mast cell growth factor and c-kit ligand in the art. SF is a transmembrane protein with a cytoplasmic domain and an extracellular domain. Soluble SF refers to a fragment cleaved from the extracellular domain at a specific proteolytic cleavage site. Membrane associated SF refers to both normal SF before it has been cleaved or the SF which has been altered so that proteolytic cleavage cannot take place.

This invention provides a non-mouse pluripotential ES cell which can be maintained on feeder layers for at least 20 passages, and give rise to embryoid bodies and multiple differentiated cell phenotypes in monolayer culture. Only those non-mouse animals which can be induced to form ES cells by the described methods are within the scope of the invention. Given the methods described herein, an ES cell can be made for any animal. However, mammals are preferred since many beneficial uses of mammalian ES cells exist. Mammalian ES cells such as rats, rabbits, guinea pigs, goats, pigs, cows, and humans can all be obtained. Alternatively, embryos from these animals can be screened for the ability to produce ES cells. While the ES cells are non-mouse, it is possible that the ES cells produced by the combination of FGF, LIF and SF physically differ from the existing established murine ES cells. Thus, murine ES cells produced by the addition of FGF, LIF and SF are also contemplated.

The ES cells of this invention can be maintained for at least 20 passages. However, the ES cells may be capable of indefinite maintenance.

Once the non-mouse ES cells are established, they can be genetically manipulated to produce a desired characteristic. For example, the ES cells can be mutated to render a gene non-functional, e.g. the gene associated with cystic fibrosis or an oncogene. Alternatively, functional genes can be inserted to allow for the production of that gene product in an animal, e.g. growth hormones or valuable proteins. Such methods are very well established in the art (Sedivy and Joyner (1992)).

The invention also provides a composition comprising:

(a) pluripotential ES cells and/or primordial germ cells and/or embryonic ectoderm cells; and (b) an FGF, LIF, membrane associated SF, and soluble SF in amounts to enhance the growth of and allow the continued proliferation of the cell.

Also provided is a composition comprising an FGF, LIF, membrane associated SF, and soluble SF in amounts to enhance the growth of and allow the continued proliferation of embryonic ectoderm or primordial germ cells.

The compositions arise from the fact that FGF, LIF and SF are used either to enhance the growth and proliferation of primordial germ cells or embryonic ectoderm cells to become ES cells. Growth and proliferation enhancing amounts can vary. Generally, 0.5 to 500 ng/ml of culture solution is adequate. Preferably, the amount is between 10 to 20 ng/ml.

Alternatively, FGF, LIF, and SF can be used to maintain ES cells. The amounts of FGF, LIF and SF necessary to maintain ES cells can be much less than that required to enhance growth or proliferation to become ES cells. In addition, FGF, LIF or SF may not be required for maintenance of ES cells.

In general, FGF or LIF from a species different from the source of the ES, primordial germ cell or embryonic ectoderm can be utilized. In addition, the SF utilized is preferably from the same species as the utilized cell type. However, FGF, LIF or SF from various species can be routinely screened and selected for efficacy in a cell from a different species.

The invention also provides a method of making a pluripotential ES cell comprising administering a growth enhancing amount of basic FGF, LIF, membrane associated SF, and soluble SF to primordial germ cells and/or embryonic ectoderm cells under cell growth conditions, thereby making a pluripotential ES cell. This method can be practiced utilizing any animal cell, especially mammal cells including mice, rats, rabbits, guinea pigs, goats, cows, pigs, humans, etc. The ES cell produced by this method is also contemplated. "Cell growth conditions" are set forth in the Examples. However, many alterations to these conditions can be made and are routine in the art.

Also provided is a method of screening cells which can be promoted to become an ES cell comprising contacting the cells with basic FGF, LIF, membrane associated SF, and soluble SF in amounts to enhance the growth of and allow proliferation of the cells and determining which cells become ES cells. Utilizing this method, cells other than primordial germ cells and embryonic ectoderm cells can be selected as a source of ES cells.

Since the invention provides ES cells generated for virtually any animal, the invention provides a method of using the ES cells to contribute to chimeras in vivo comprising injecting the cell into a blastocyst and growing the blastocyst in a foster mother. Alternatively, aggregating the cell with a morula stage embryo and growing the embryo in a foster mother can be used to produce a chimera. As discussed above, the ES cells can be manipulated to produce a desired effect in the chimeric animal. The methods of producing such chimeric animals are well established (Robertson (1987)).

Alternatively, the ES cells can be used to derive cells for therapy to treat an abnormal condition. For example, derivatives of human ES cells could be placed in the brain to treat a neurodegenerative disease.

FGF, SF and LIF have been shown herein to be critical for making ES cells. However, as noted above for FGF, other members of the respective growth factor family could also be used to make ES cells. Thus, later discovered members of each family can merely be substituted to determine if the new factor enhances the growth and allows the continued proliferation of PGCs or embryonic ectoderm cells to form ES cells. For example, if a new member of the LIF family is discovered, the new LIF is merely combined with SF and FGF to determine if the new family member enhances the growth and allows the continued proliferation of PGCs or embryonic ectoderm cells. Thus, this invention provides the use of family members and a method of screening family members for activity.

Likewise, additional growth factors may be found useful in enhancing the growth and proliferation of PGCs or embryonic ectoderm cells from various animals. This invention provides combining FGF, SF and LIF with other growth factors to obtain or enhance the production of ES cells. Thus, a method of screening other growth factors for the ability to promote PGCs and embryonic ectoderm cells to form ES cells is also provided. In this regard, IL-11 and IL-6 are good screening candidates and can be used to promote ES cell formation.

EXAMPLES

All the cell types and other materials listed below can be obtained through available sources and/or through routine methods.

MATERIALS AND METHODS

Feeder cells

The Sl/Sl$^4$ cell line, derived from a homozygous null Sl/Sl mouse embryo, and its derivative, Sl$^4$-m220, which stably expresses only membrane bound murine SF lacking exon 6 encoding the proteolytic cleavage site, were obtained from Dr. David Williams (Howard Hughes Medical Institute, Indiana University Medical School). Other cell lines which produce adequate SF can be substituted for Sl/Sl$^4$. They were maintained in DMEM with 10% calf serum and 50 ug/ml gentamicin. For making feeder layers they were irradiated (500 rads) and plated at a density of 2×105 per well of 24-well plates (Falcon) in the same medium, 24 hrs before use. Wells were pre-treated with 1% gelatin. STO cells stably transfected with human LIF and the bacterial neor gene (SLN) were obtained from Dr. Allan Bradley.

Primary cultures of PGCs

Embryos were from ICR females mated with (C57BLxDBA) F1 males. Noon of the day of plug is 0.5 day post coitum (p.c.). The caudal region of 8.5 day p.c. embryos (between the last somite and the base of the allantois) was dissociated into single cells by incubation at 37° C. with 0.05% trypsin, 0.02% EDTA in Ca++/Mg++ free Dulbecco's phosphate-buffered saline (PBS) for about 10 mins with gentle pipetting. At this stage there are between about 149 and 379 PGCs in each embryo (Mintz and Russell, 1957). Cells from the equivalent of 0.5 embryo were seeded into a well containing feeder cells as above and 1 ml of DMEM, 2 mM glutamine, 1 mM sodium pyruvate, 100 i.u./ml penicillin and 100 ug/ml streptomycin and 15% fetal bovine serum (PGC culture medium). Finely minced fragments of genital ridges from 1.5 and 12.5 day p.c. embryos were trypsinized as above and plated at a concentration of 0.1 embryo per well. Growth factors were added at the time of seeding, usually at the following concentrations, which were shown to be optimal for PGC proliferation; recombinant human LIF and bFGF (10–20 ng/ml) and soluble rat SF (60 ng/ml). The medium was changed every day.

Secondary culture of PGC

Primary cultures were trypsinized and reseeded into wells containing Sl$^4$-m220 feeder layers in PGC culture medium. For further subculture, rounded colonies of densely packed ES-like cells were carefully picked up in a finely drawn pipette and trypsinized in a microdrop under mineral oil before seeding into wells containing feeder cells as above. After several subcultures in this way, cultures were passaged without picking individual colonies.

Alkaline phosphatase (AP) staining

This was carried out as described (Matsui et al. 1991). After staining, AP positive cells were counted using an inverted microscope.

SSEA-1 staining

PGC cultures on Sl$^4$-m220 feeder cells on a chamber slide (Nunc) were washed twice with PBS containing 2% calf serum, 0.1% sodium azide and then incubated with mouse monoclonal antibody SSEA-1 (1:100 dilution) on ice for 30 min. After washing with PBS, cells were incubated for 30 mins with FITC-conjugated Fab' fragment of goat anti mouse IgG (H+L) (Cappell, 1:5 dilution). After washing in PBS, cells were fixed in 4% paraformaldehyde before staining for AP.

Tumors in nude mice

Approximately 2×106 cells from three independent lines were injected subcutaneously into nude mice (three mice per line). After three weeks tumors were fixed in Bouin's fixative, processed for histology and sections stained with haematoxylin and eosin.

Chimera formation

Ten to fifteen cells from two independent lines derived from 8.5 day p.c. embryos were injected into the blastocoel of 3.5 day p.c. blastocysts of either ICR or C57BL/6 mice. These were returned to the uteri of 2.5 day p.c. pseudopregnant foster mothers.

Culture of murine PGCs in the presence of growth factors

Figure 1A:
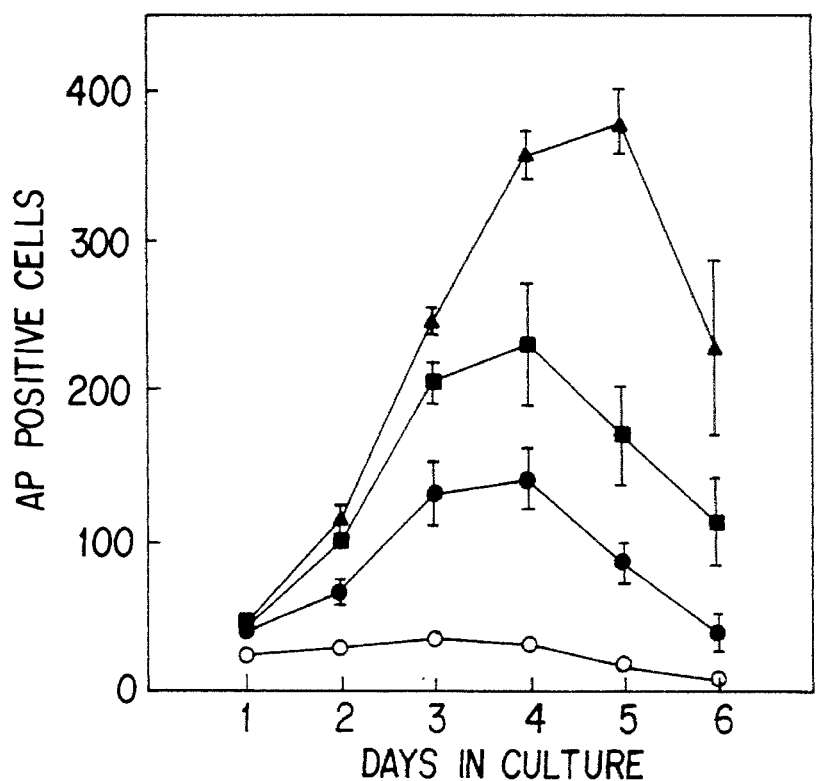
FIG. 1 shows the effect of growth factors on murine PGCs in culture.
Figure 1B:
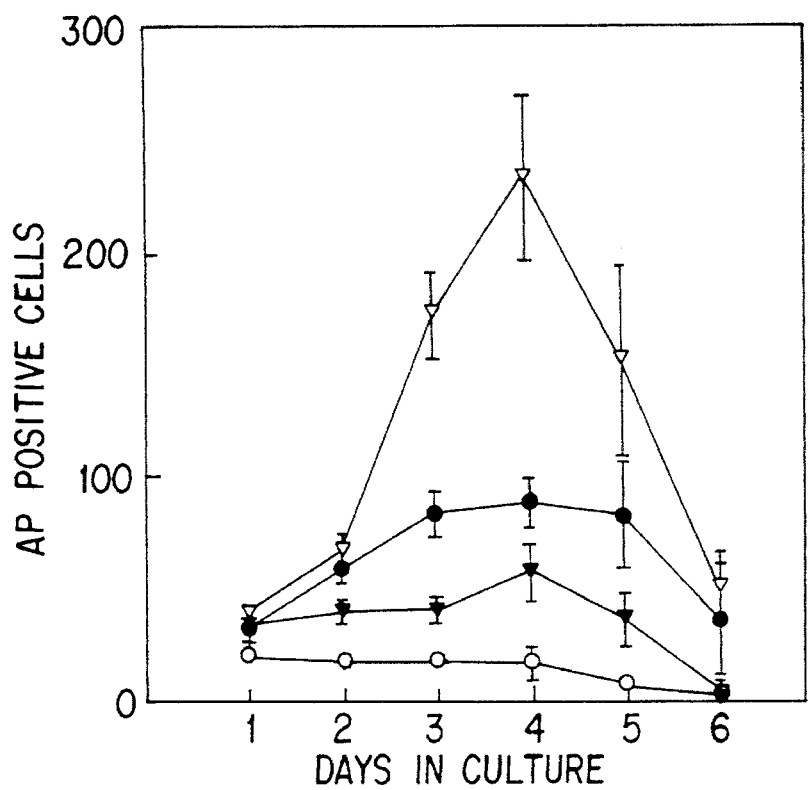

Initial experiments used Sl/Sl$^4$ cells derived from a homozygous null Sl/Sl mutant mouse as a feeder layer for the culture of cells dissociated from the posterior of 8.5 days p.c. embryos, and AP staining as a marker for PGCs (FIG. 1A). As shown previously (Matsui et al., 1991), soluble SF and LIF act synergistically on PGCs. Addition of bFGF further enhances growth, and the cells continue to increase in number until day 5 in culture, i.e. one day longer than usual. The effect of bFGF alone is small, and both SF and LIF are needed in addition to bFGF for maximal effect on PGC growth (FIG. 1A, B). A variety of other growth factors, including human activin, Bone Morphogenetic Protein-4, βNGF, and PDGF at 10 and 50 ng/ml had no effect in the presence of SF and LIF.

Figure 1C:
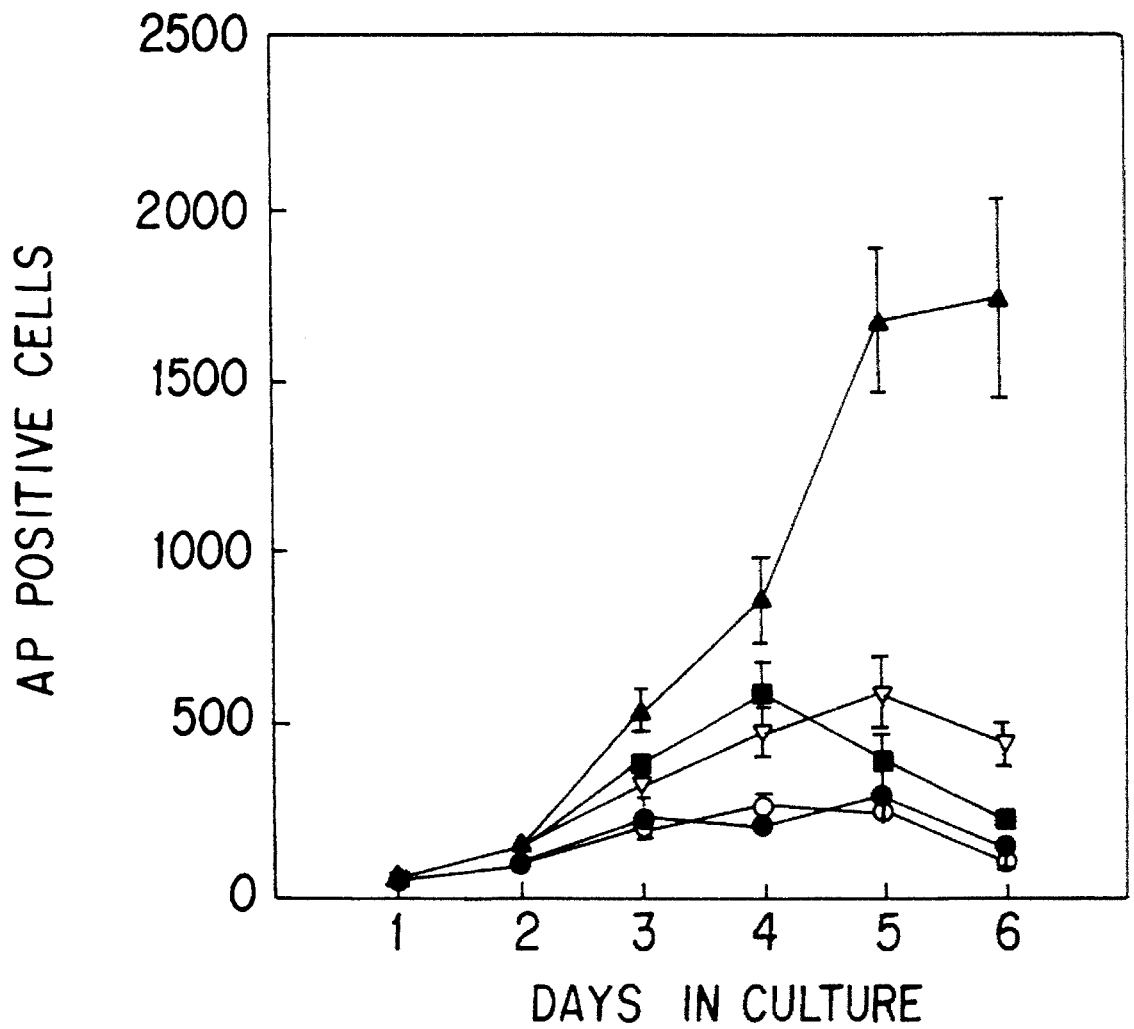

Membrane associated SF seems to play an important role in PGC proliferation since Sl$^d$ mouse mutants which make only soluble SF have a reduced number of PGCs in vivo, and membrane associated SF is more effective than soluble SF in supporting PGC growth and survival in culture (Dolci et al., 1991; Matsui et al., 1991). To test the effect of added factors in the presence of membrane associated SF, 8.5 day p.c. PGCs were cultured on Sl$^4$-m220 feeder cells, which express only membrane associated SF (Matsui et al., 1991; Toksoz et al., 1991). Both LIF and bFGF separately enhance PGC growth on Sl$^4$-m220 feeder cells with added soluble rSF. However, when LIF and bFGF are added together, PGC growth is dramatically stimulated and the cells continue to proliferate through to day 6 in culture (FIG. 1C). The cells survive until day 8, at which time the feeder layer deteriorates, but they can be trypsinized and subcultured (see below).

Figure 2A:
Figure 2D:
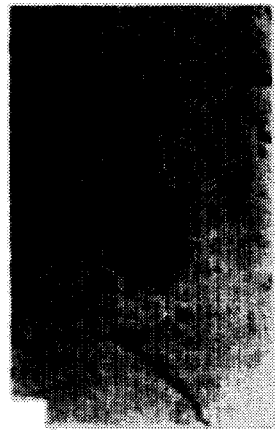
Figure 2G:
Figure 2B:
Figure 2E:
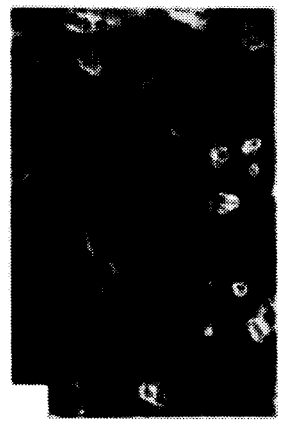
Figure 2H:
Figure 2C:

Pregonadal PGCs are motile in vivo, and when cultured with LIF on a Sl$^4$-m220 feeder layer they form burst colonies of cells with a flattened and polarized morphology, characteristic of motile cells (FIG. 2A). In contrast, PGCs cultured on a Sl$^4$-m220 feeder layer with soluble SF and bFGF or with bFGF and LIF (FIGS. 2B, C), form discrete colonies of tightly packed cells. These colonies increase in size over day 6 in culture only when both bFGF and LIF are present (FIG. 2C).

To determine whether PGCs and their descendants continue to proliferate in culture, primary colonies of PGCs were trypsinized after 6 days in culture and replated on a fresh Sl$^4$-m220 feeder layer with added growth factors. By day 6 in secondary culture, large colonies of densely packed AP positive cells resembling embryonic stem (ES) cells are present (FIGS. 2D, E; FIGS. 4, A), with an overall plating efficiency of about 5%. These colonies are also positive for the expression of the antigen SSEA-1, a characteristic of PGCs (Donovan et al., 1986) and undifferentiated embryonal carcinoma and ES cells (Solter and Knowles, 1978) (FIGS. 2G, H). Although the growth of primary cultures is strictly dependent on the presence of LIF and bFGF, secondary colonies can form in the absence of these factors (Table 1), indicating a reduced exogenous growth factor requirement for the descendants of PGCs after subculture. Most of the colonies show strong, uniform AP staining. However, some colonies contain only a small number of strongly stained cells, surrounded by cells which are weakly stained or negative (FIG. 2E). In many cases these negative cells are larger and have a more flattened morphology than the AP positive cells. For further subculture, individual colonies of cells with a distinctive, tightly packed, ES cell-like morphology were picked up in a micropipet, trypsinized and replated on a fresh feeder layer with added factors. Such colonies can be subcultured at least ten times and continue to give rise to colonies of similar morphology. In later passages, these cultures were transferred to feeder layers of STO cells in medium without added factors normally used for blastocyst-derived ES cell culture (Robertson, 1987). Under these conditions they continue to proliferate in an undifferentiated state, for a total of at least 20 passages.

Two independent lines at passage 14 (1/14, 2/14) and one at passage 20 (3/20) were karyotyped. Most cells had a normal or near normal XY karyotype, but in two lines (2/14 and 3/20) there was a significant proportion of trisomic cells.

Long term culture of PGC-derived cells from genital ridges

Figure 2F:
Figure 2I:
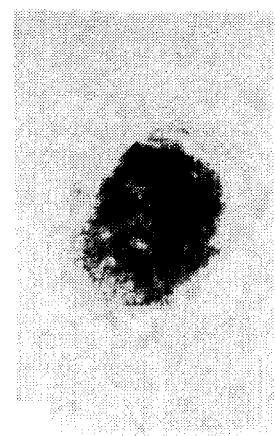

Since transplantable teratocarcinomas can be induced experimentally by grafting genital ridges from 11.5 or 12.5 days p.c. male embryos of the 129 strain to an ectopic site, we tested the possibility that ES-like cells can be obtained from genital ridges in culture. Genital ridges were trypsinized and the cells plated on an Sl$^4$-m220 feeder layer with soluble SF, LIF and bFGF. The number of PGCs initially declines but increases after 3 days, and by 6 days colonies of densely packed, AP positive cells can be seen (FIG. 2F). If cells from male and female 12.5 days p.c. genital ridges are cultured separately, male PGCs increase in number and form colonies. In contrast, only a few female PGCs form colonies (FIG. 3). The differentiation capacity of genital ridge-derived colonies has not so far been tested.

Differentiation of PGC-derived ES cells in vitro and in nude mice

Four independent lines of undifferentiated cells derived from 8.5 day embryos and cultured onto STO feeder layers were trypsinized and pipetted gently to generate small clumps of cells which were then placed in bacteriological plastic dishes. After five to seven days most of the clumps differentiated into typical simple or cystic embryoid bodies (EBs), with a clear outer layer of extraembryonic endoderm cells (FIGS. 4, B). When these EBs were returned to tissue culture plastic dishes they rapidly attached and over two weeks gave rise to a variety of cell types, including extraembryonic endoderm, spontaneously contracting muscle, nerve and endothelial and fibroblast-like cells.

Three of these four lines, at passages 9 and 15 on STO cells, were injected subcutaneously into nude mice. Each line gave rise to multiple, well-differentiated teratocarcinomas, containing a wide variety of tissues, including keratinized, secretory and ciliated epithelium, neuroepithelium and pigmented epithelium, cartilage, bone, and muscle, as well as nests of undifferentiated embryonic cells (FIGS. 4, C–E).

PGC-derived ES cells can contribute to chimeras in vivo

To test whether the descendants of PGCs in culture are able to contribute to chimeras in vivo, 10–15 cells with an ES-like morphology from two independent early passage cultures derived from 8.5 day embryos and cultured on either Sl$^4$m220 cells or STO cells were injected into host ICR or C57BL/6 blastocysts. From a total of 21 pups born, four were chimeric, as judged by coat color, but only two were extensive, with approximately 50 and 90% chimerism. The 50% coat color chimera, generated by injecting cells from the 4th passage on STO cells into an ICR blastocyst, died at 11 days after birth and showed stunted growth and skeletal abnormalities. The 90% coat color chimera, obtained by injecting cells from the 6th passage on STO cells into a C57BL/6 blastocyst, had no obvious abnormalities.

Generation of ES cells from other mammals

ES cells from other mammals can be produced using the methods described above for murine. The mammalian cell of choice is simply substituted for murine and the murine methods are duplicated. The appropriate species specific growth factors (e.g. SF) can be substituted for murine growth factors as is necessary. Any additional growth factors which can promote the formation of ES cells can be determined by adding the growth factors to FGF, LIF, and SF as described above and monitored for an affect on ES formation.

Generation of chimeras using non-murine ES cells

Chimeras utilizing non-murine ES cells can likewise be produced utilizing the methods for murine described above and simply substituting the appropriate non-murine blastocyst for the species of ES utilized.

Throughout this application various publications are referenced. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

TABLE 1

| | Growth Factor Requirements for Secondary Cultures of PCG-Derived Cells | | |
|---|---|---|---|
| Days in Culture | SF→SF+LIF+LIF+ bFGF | SF+LIF+bFGF→SF+ LIF+bFGF | SF+ LIF+bFGF→SF |
| 1 | 112 ± 16 cells | 116 ± 20 cells | 142 ± 18 cells |
| 3 | 0.9 ± 0.6 colonies | 4.6 ± 1.1 colonies | 5.6 ± 0.8 colonies |
| 5 | 0.5 ± 0.4 colonies | 6.9 ± 1.2 colonies | 6.6 ± 1.3 colonies |

PGCs from 8.5 dpc embryos were cultured for 6 days on $Sl^4$-m220 cells in the presence of either soluble rat SF alone or with soluble rat SF, LIF, and bFGF. Cultures were trypsinized and seeded into wells containing $Sl^4$-m220 feeder cells with either soluble rat SF alone or soluble rat SF, LIF, and bFGF. Cultures were fixed and AP-positive cells (day 1) or colonies (days 2 and 5) counted. Numbers are mean ± SEM from four experiments. Secondary cultures show a reduced growth factor requirement compared with primary cultures.

REFERENCES

Bogler, O., Wren, D., Barnett, S. C., Land, H. and Noble, M. (1990). Cooperation between two growth factors promotes extended self-renewal and inhibits differentiation of oligodendrocyte-type-2 astrocyte (O-2A) progenitor cells. Proc. Natl. Acad. Sci. USA. 87, 6368–6372.

Dolci, S., Williams, D. E., Ernst, M. K., Resnick, J. L., Brannan, C. I., Lock, L. F., Lyman, S. D., Boswell, H. S. and Donovan, P. J. (1991). Requirement for mast cell growth factor for primordial germ cell survival in culture. Nature 352, 809–811.

Donoran, P. J., Stott, D., Cairns, L. A., Heasman, J. and Wylie, C. C. (1986). Migratory and postmigratory mouse primordial germ cells behave differenetly in culture. Cell 44, 831–838.

French-Constant, C., Hollingsworth, A., Heasman, J. and Wylie, C. C. (1991). Response to fibronectin of mouse primordial germ cells before, during and after migration. Development 113, 1365–1373.

Godin, I. and Wylie, C. C. (1991). TGFB-1 inhibits proliferation and has a chemotropic effect on mouse primordial germ cells in culture. Development 113, 1451–1457.

Godin, I., Deed, R., Cooke, J., Zsebo, K., Dexter, M. and Wylie, C. C. (1991). Effects of the steel gene product on mouse primordial germ cells in culture. Nature 352, 807–809.

Ginsberg, M., Snow, M. H. L. and McLaren, A. (1990). Primordial germ cells in the mouse embryo during gastrulation. Development 110, 521–528.

Lawson, K. A. and Pederson, R. A. (1992). Clonal analysis of cell fate during gastrulation and early neurulation in the mouse in CIBA Foundation Symposium 165 Post Implantation Development in the Mouse John Wiley and Sons.

Mann, J. R., Gadi, I., Harbison, M. L., Abbondanzo, S. J. and Stewart, C. L. (1990). Androgenetic mouse embryonic stem cells are pluripotent and cause skeletal defects in chimeras: implications for genetic imprinting. Cell 62, 251–260.

Manova, K. and Bachvarova, R. F. (1991). Expression of c-kit encoded at the W locus of mice in developing embryonic germ cells and presumptive melanoblasts. Dev. Biol. 146, 312–324.

Matsui, Y., Toksok, D., Nishikawa, S., Nishikawa, S-I,

Williams, D., Zsebo, K. and Hogan, B. L. M. (1991). Effect of steel factor and leukemia inhibitory factor on murine primordial germ cells in culture. Nature 353, 750–752.

Mintz, B. and Russell, E. S. (1957). Gene-induced embryological modifications of primordial germ cells in the mouse. J. Exp. Zoology 134, 207–230.

Noble, M., Murray, K., Stroobant, P., Waterfield, M. D. and Riddle, P. (1988). Platelet-derived growth factor promotes division and motility and inhibits premature differentiation of the oligodendrocyte/type-2 astrocyte progenitor cell. Nature 333, 560–562.

Noguchi, T. and Stevens, L. C. (1982). Primordial germ cell proliferation in fetal testes in mouse strains with high and low incidences of congenital testicular teratomas J. Natl. Cancer Inst. 69, 907–913.

Raff, M. C., Lillien, L. E., Richardson, W. D., Burne, J. F. and Noble, M. D. (1988). Platelet-derived growth factor from astrocytes drives the clock that times oligodendrocyte development in culture. Nature 333, 562–565.

Robertson, E. J. (1987). Embryo-derived stem cell lines in teratocarcinomas and embryonic stem cells: a practical approach. Ed. E. J. Robertson, IRL Press, Oxford pp. 71–112.

Robertson, E. J. (1987). Teratocarcinomas and embryonic stem cells: a practical approach, Ed. E. J. Robertson, IRL Press, Oxford.

Sedivy, J. M., and A. Joyner (1992). Gene Targeting, W. H. Freeman and Co.

Solter, D., Adams, N., DamJanov, I. and Koprowski, H. (1975). Control of teratocarcinogenesis in teratomas and differentiation, Eds. M. I. Sherman and D. Solter, Academic Press.

Solter, D. and Knowles, B. B. (1978). Monoclonal antibody defining a stage-specific mouse embryonic antigen (SSEA-1) Proc. Natl. Acad. Sci. USA 75, 5565–5569.

Soriano, P. and Jaenisch, R. (1986). Retroviruses as probes for mammalian development: allocation of cells to the somatic and germ cell lineages. Cell 46, 19–29.

Stevens, L. C. (1983). The origin and development of testicular, ovarian, and embryo-derived teratomas. Cold Spring Harbor Conferences on Cell Proliferation Vol. 10 Teratocarcinoma Stem Cells. Eds. Silver, L. M., Martin, G. R. and S. Strickland. 10, 23–36.

Stevens, L. C. and Makensen, J. A. (1961). Genetic and environmental influences on teratogenesis in mice. J. Natl. Cancer Inst. 27, 443–453.

Surani, M. A., Kothary, R., Allen, N. D., Singh, P. B., Fundele, R., Ferguson-Smith, A. C. and Barton, S. C. (1990). Genome imprinting and development in the mouse development. Suppl., 89–98.

Tam, P. P. L. and Snow, M. H. L. (1981). Proliferation and migration of primordial germ cells during compensatory growth in mouse embryos. J. Embryol. Exp. Morph. 64, 133–147.

Toksoz, D., Zsebo, K. M., Smith, K. A., Hu, S., Brankow, D., Suggs, S. V., Martin, F. H. and Williams, D. A. (1992). Support of human hematopoiesis in long-term bone marrow cultures by murine stromal cells selectively expressing the membrane-bound and secreted forms of the human homolog of the steel product, stem cell factor. Proc. Natl. Acad. Sci. USA, in press.

Yamaguchi, T. P., Conlon, R. A., and J. Rossant (1992). Expression of the fibroblast growth factor receptor FGFR-1/flg during gastrulation and segmentation in the mouse embryo. Development 152:75–88.

What is claimed is:

1. A composition comprising:
   (a) pluripotential embryonic stem cells; and
   (b) a fibroblast growth factor, leukemia inhibitory factor, membrane associated steel factor, and soluble steel factor in amounts to enhance the growth of and allow the continued proliferation of the cells.

2. The composition of claim 1, wherein the fibroblast growth factor is basic fibroblast growth factor.

3. A composition comprising:
   (a) primordial germ cells; and
   (b) a fibroblast growth factor, leukemia inhibitory factor, membrane associated steel factor and soluble steel factor in amounts to enhance the growth of and allow the continued proliferation of the cells.

4. The composition of claim 3, wherein the fibroblast growth factor is basic fibroblast growth factor.

5. A composition comprising:
   (a) embryonic ectoderm cells; and
   (b) fibroblast growth factor, leukemia inhibitory factor, membrane associated steel factor and soluble steel factor in amounts to enhance the growth of and allow the continued proliferation of the cells.

6. A composition comprising a fibroblast growth factor, leukemia inhibitory factor, membrane associated steel factor, and soluble steel factor in amounts to enhance the growth of and allow the continued proliferation of primordial germ cells.

7. The composition of claim 6, wherein the fibroblast growth factor is basic fibroblast growth factor.

8. A method of making a pluripotential embryonic stem cell comprising administering a growth enhancing amount of basic fibroblast growth factor, leukemia inhibitory factor, membrane associated steel factor, and soluble steel factor to primordial germ cells under cell growth conditions, thereby making a pluripotential embryonic stem cell.

9. The method of claim 8 wherein the stem cell is derived from a mammal.

10. The method of claim 9, wherein the mammal is a mouse.

11. A method of making a pluripotential embryonic stem cell comprising administering a growth enhancing amount of basic fibroblast growth factor, leukemia inhibitory factor, membrane associated steel factor, and soluble steel factor to embryonic ectoderm cells under cell growth conditions, thereby making a pluripotential embryonic stem cell.

12. The method of claim 11, wherein the stem cell is derived from a mammal.

13. A method of screening cells which can be promoted to become pluripotent embryonic stem cells comprising contacting the cells with basic fibroblast growth factor, leukemia inhibitory factor, membrane associated steel factor, and soluble steel factor in amounts to enhance the growth of and allow proliferation of the cells and determining which cells become pluripotent embryonic stem cells.

14. A composition comprising a fibroblast growth factor, leukemia inhibitory factor, membrane associated steel factor, and soluble steel factor in amounts to promote the formation of pluripotent embryonic stem cells from primordial germ cells.

* * * * *